United States Patent [19]

Reap

[11] Patent Number: 4,566,898

[45] Date of Patent: * Jan. 28, 1986

[54] HERBICIDAL SULFONAMIDES

[75] Inventor: James J. Reap, Wilmington, Del.

[73] Assignee: E. I. Du Pont de Nemours and Company, Wilmington, Del.

[*] Notice: The portion of the term of this patent subsequent to May 10, 2000 has been disclaimed.

[21] Appl. No.: 648,065

[22] Filed: Sep. 7, 1984

[51] Int. Cl.$^4$ .................. C07D 251/42; C07D 251/16; A01N 43/66
[52] U.S. Cl. ......................................... 71/93; 544/211
[58] Field of Search ............................ 71/93; 544/211

[56]        References Cited
U.S. PATENT DOCUMENTS
4,383,113  5/1983  Levitt .................................. 544/211

Primary Examiner—John M. Ford

[57]            ABSTRACT

4-Chloro-2-[[(4-methoxy-6-methyl-1,3,5-triazin-2-yl)aminocarbonyl]aminosulfonyl]benzoic acid (1-methylethyl) ester has unexpectedly been discovered to be an outstanding agricultural chemical. The compound is a highly active preemergent and/or postemergent herbicide. The invention includes the compound, compositions containing the compound, and its method-of-use as an agricultural chemical.

5 Claims, No Drawings

HERBICIDAL SULFONAMIDES

BACKGROUND OF THE DISCLOSURE

This invention pertains to the compound 4-Chloro-2-[[[(4-methoxy-6-methyl-1,3,5-triazin-2-yl)-aminocarbonyl]aminosulfonyl]benzoic acid, (1-methylethyl)ester, its agriculturally suitable salts, agricultural compositions containing the compound, and its method-of-use as a selective preemergent and/or postemergent herbicide.

The compound of the instant invention is generically disclosed in U.S. Pat. No. 4,383,113 which discloses herbicidal benzenesulfonamides of the following formula:

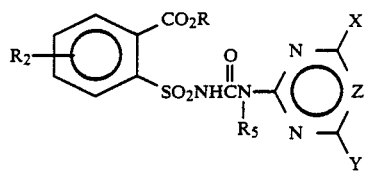

There is no specific teaching to the compound of the instant invention and its use on blackgrass although, as mentioned above, it is generically disclosed.

SUMMARY OF THE INVENTION

This invention pertains to the novel compound of Formula I, its agriculturally suitable salts, agricultural compositions and its method-of-use as a selective preemergent and/or postemergent herbicide. The compound is especially useful for the control of blackgrass in wheat or barley. Blackgrass is a particularly difficult weed to control.

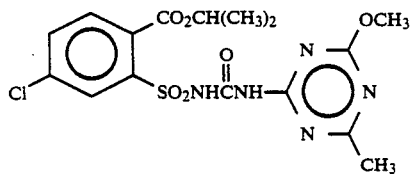

I

4-Chloro-2-[[[(4-methoxy-6-methyl-1,3,5-triazin-2-yl)aminocarbonyl]aminosulfonyl]benzoic acid (1-methylethyl)ester, m.p. 165°–166° C.

DETAILED DESCRIPTION OF THE INVENTION

The compound of this invention, Formula I, can be prepared by the method described in Equation 1.

EQUATION 1

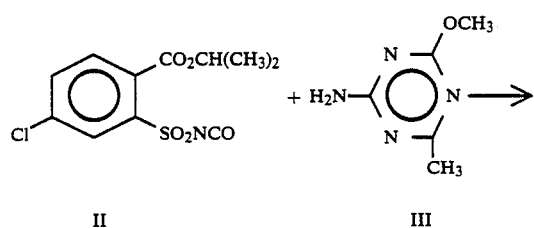

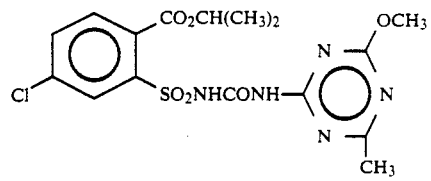

I

The sulfonylisocyanate of Formula II is reacted with the triazinamine of Formula III in an inert solvent such as methylene chloride, acetonitrile, xylene or chlorobenzene, for a period of 1 to 96 hours at temperatures of about 20° to 100° C. The product of Equation 1 can be isolated either by filtration or by evaporation of the reaction solvent, and trituration with a solvent such as 1-chlorobutane, ether or similar solvents.

The sulfonylisocyanate of Formula II can be prepared by methods, or modifications thereof obvious to one skilled in the art, described in U.S. Pat. No. 4,379,769.

The compound of Formula I can also be prepared by the method shown in Equation 2 by reacting the sulfonamide of Formula IV with the phenylcarbamate of Formula V in the presence of a molar equivalent of 1,8-diazabicyclo[5.4.0]undec-7-ene. The phenyl carbamate of Formula V can be prepared by the reaction of the triazinamine of Formula III with diphenyl carbonate in the presence of a base such as sodium hydride or alternatively, by the reaction of the triazinamine of Formula III with phenylchloroformate in the presence of an acid acceptor such as pyridine or triethylamine.

EQUATION 2

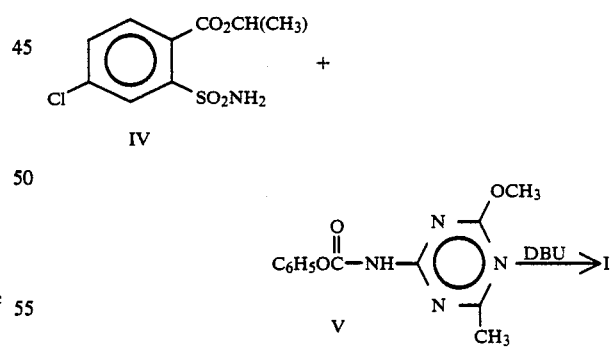

Also, the compound of Formula I can be prepared, as shown in Equation 3, by reacting the triazinamine of Formula III with phenylcarbamate of Formula VI at temperatures of about 25° to 100° C. in solvents such as dioxane, acetonitrile or tetrahydrofuran for a period of about 1 to 24 hours. The phenyl carbamate of Formula VI can be prepared by reaction of the sulfonamide of Formula IV with phenyl chloroformate in the presence of a base such as pyridine or sodium hydroxide.

EQUATION 3

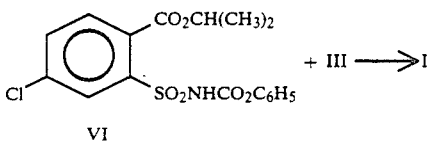

The sulfonamide of Formula IV can be prepared by reacting the benzothiazol-3-one-1,1-dioxide of Formula VII with 2-propanol in the presence of an acid catalyst such as hydrogen chloride, as shown in Equation 4.

EQUATION 4

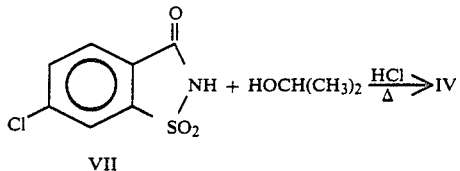

The amine of Formula III can be prepared by the method of Hoffmann and Schaeffer, *J. Org. Chem.*, 28, 1916 (1963).

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide, carbonate or hydroxide). Quaternary amine salts can be made by similar techniques.

Salts of the compound of Formula I can also be prepared by exchange of one cation for another. Cationic exchange can be effected by direct contact of an aqueous solution of a salt of the compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of the compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble.

Acid addition salts, useful in this invention, can be obtained by reacting the compound of Formula I with a suitable acid, e.g., p-toluenesulfonic acid, trichloroacetic acid or the like.

The compound of this invention and its preparation is further illustrated by the following examples wherein temperatures are given in degrees centigrade unless otherwise designated.

EXAMPLE 1

5-Chloro-2-Methylbenzenesulfonylchloride

5-Chloro-2-methylbenzeneamine (1002 g) was added over 0.5 hr. to a stirred mixture of 5.5 L of concentrated hydrochloric acid and 1.5 L of acetic acid precooled to 0°–5° C. The resulting suspension was stirred 0.5 hr. A solution of 530 g of sodium nitrite in 0.9 L $H_2O$ was added over 1.0 hr. while maintaining the temperature at 0°–5° C. When addition was complete, the mixture was stirred 1.0 hr. at 0°–5° C. The diazonium salt was added to a stirred mixture of 6.0 L of acetic acid, 1000 g of sulfur dioxide and 16.8 g of cuprous chloride while maintaining the temperature about 15° C. When addition of the diazonium salt was complete, the mixture was stirred several hours at about 15° C. then allowed to warm to ambient temperature and stirred overnight. The reaction mixture was poured into ice-water, and the aqueous mixture was extracted with 12 L of methylene chloride. The organic solution was washed twice with 6 L water followed twice with 4 L of saturated sodium bicarbonate solution. The organic solution was dried over magnesium sulfate, filtered and the solvent evaporated in vacuo to give 1279.9 g of the title compound as a black oil.

EXAMPLE 2

5-Chloro-2-methylbenzenesulfonamide

A solution of 3810.5 g of 5-chloro-2-methylbenzenesulfonyl chloride in 10.8 L of tetrahydrofuran was cooled to 0°–5° C. and 720 g of anhydrous ammonia was added while maintaining the temperature at 0°–5° C. When addition was complete, the suspension was stirred several hours at 0°–5° C., then allowed to warm to ambient temperature overnight. The precipitated ammonium chloride was filtered and washed with tetrahydrofuran. The filtrate was concentrated in vacuo until solids were formed. The solids were collected, washed with 1-chlorobutane and dried to give 2449 g of the title compound, m.p. 142°–145° C.

EXAMPLE 3

6-Chloro-1,2-benzothiazole-3-one,1,1-dioxide

Potassium permanganate (190 g) was added in one portion to a stirred mixture of 132 g of 5-chloro-2-methylbenzenesulfonamide, 25 g of sodium hydroxide and 300 mL of water. The mixture was heated to 50° C. over 2 hrs. and held at 50° C. for an additional 27 hrs. The mixture was cooled to ambient temperature and 12 g of sodium bisulfite was added. After stirring 0.25 hr., the reaction mixture was filtered through a pad of Celite ®. The filtrate was acidified to pH 6.0 with hydrochloric acid. The resulting solid was collected, washed with water, and dried to give 20.1 g of recovered 5-chloro-2-methylbenzenesulfonamide. The filtrate was acidified to pH 1.0 with hydrochloric acid. The solid was collected, washed with water and dried to give 83.9 g of the title compound, m.p. 216°–220° C.

EXAMPLE 4

(1-Methylethyl)-2-(aminosulfonyl)-4-chlorobenzoate

Anhydrous hydrogen chloride was passed into a mixture of 773.7 g of 6-chloro-1,2-benzothiazole-3-one-1,1-dioxide and 7 L of 2-propanol until the mixture was saturated (7.5 hr.). The mixture was heated at reflux (80° C.) for 1.5 hr., then cooled to 0° C. The precipitated solids were collected and dried to give 893.9 g of the title compound, m.p. 143°–145° C. A second crop (44.5 g, m.p. 140°–142° C.) and third crop (125 g, m.p. 133°–135° C.) were obtained by concentrating the mother liquors in vacuo.

EXAMPLE 5

(1-Methylethyl)-2-[(butylaminocarbonyl)aminosulfonyl]-4-chlorobenzoate

A mixture of 1063.4 g of (1-methylethyl)-2-(aminosulfonyl)-4-chlorobenzoate, 590.4 g of butylisocyanate, 590.4 g of potassium carbonate and 10.8 L of 2-butanone was heated at reflux overnight. After cooling to ambient temperature, the reaction mixture was divided into two portions. Each portion was poured into 10 L of ice-water. The aqueous mixtures were extracted with 9 L each of methylene chloride. The combined aqueous phases were acidified to pH 1.0 with concentrated hydrochloric acid. The resulting solids were collected and dried to give 714.6 g of the title compound, m.p. 129°-132° C.

EXAMPLE 6

(1-Methylethyl)-4-chloro-2-(isocyanatosulfonyl)benzoate

A mixture of 388.2 g (1-methylethyl)-2-[(butylaminocarbonyl)aminosulfonyl]-4-chlorobenzoate and 3 L of xylene was azeotropically dried, then cooled to ~100° C. and 1.0 g of 1,8-diazabicyclo[2.2.2.]octane was added. The mixture was heated to ~141° C. and the addition of liquefied phosgene was begun. After 90 ml of phosgene had been added, the reaction temperature was 128° C. The temperature had risen to 132° C. after 1 hr., and an additional 10 ml phosgene was added. Heating was continued the remainder of the day, then the reaction mixture was allowed to cool overnight under a nitrogen atmosphere. The following morning, the reaction mixture was heated to reflux (133° C.) and 24 ml of phosgene was added over 1 hr. The mixture was heated an additional 2 hrs. (temperature—124° C.) and then cooled to ambient temperature. The reaction mixture was filtered under nitrogen, and the filtrate was concentrated in vacuo. The title compound (400.1 g) was isolated as an oil of sufficient purity for the subsequent coupling reaction.

EXAMPLE 7

4-Chloro-2-[[(4-methoxy-6-methyl-1,3,5-triazin-2-yl)aminocarbonyl]aminosulfonyl]benzoic acid, (1-methylethyl)ester Under a nitrogen atmosphere, (1-methylethyl)-4-chloro-2-(isocyanatosulfonyl)benzoate (388.1 g) was added slowly to a stirred suspension of 143.2 g 4-methoxy-6-methyl-1,3,5-triazin-2-amine in 1280 mL of dry acetonitrile; the addition caused an exotherm of 7° C. The resulting mixture was stirred at ambient temperature for 3 days. The mixture was filtered under a nitrogen atmosphere, and the filter cake was washed with methylene chloride. The methylene chloride solution was concentrated in vacuo to give 188.9 g of the title compound, m.p. 165°-166° C. The original acetonitrile filtrate was concetrated in vacuo, and the resulting oil was triturated with ether to given an additional 64.7 g of the title compound, m.p. 154°-159° C.

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE I

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Agueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 8

Wettable Powder

4-Chloro-2-[[(4-methoxy-6-methyl-1,3,5-triazin-2-yl)aminocarbonyl]aminosulfonyl]benzoic acid, (1-methylethyl)ester: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 9

Wettable Powder

4-Chloro-2-8 [(4-methoxy-6-methyl-1,3,5-triazzin-2-yl)aminocarbonyl]aminosulfonyl]benzoic acid, (1-methylethyl)ester: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 10

Granule

Wettable Powder of Example 9: 5%
attapulgite granules (U.S.S. 20–40 mesh; 0.84–0.42 mm): 95%

A slurry of wettable powder containing 25% solids is sprayed on the surface of attapulgite granules in a double-cone blender. The granules are dried and packaged.

EXAMPLE 11

Extruded Pellet

4-Chloro-2-[[(4-methoxy-6-methyl-1,3,5-triazin-2-yl)aminocarbonyl]aminosulfonyl]benzoic acid, (1-methylethyl)ester: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

Oil Suspension

4-Chloro-2-[[(4-methoxy-6-methyl-1,3,5-triazin-2-yl)aminocarbonyl]aminosulfonyl]benzoic acid, (1-methylethyl)ester: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 13

Wettable Powder

4-Chloro-2-[[(4-methoxy-6-methyl-1,3,5-triazin-2-yl)aminocarbonyl]aminosulfonyl]benzoic acid, (1-methylethyl)ester: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

Low Strength Granule

4-Chloro-2-[[(4-methoxy-6-methyl-1,3,5-triazin-2-yl)aminocarbonyl]aminosulfonyl]benzoic acid, (1-methylethyl)ester: 1%
N,N-dimethylformamide: 9%
attapulgite granules (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 15

Aqueous Suspension

4-Chloro-2-[[(4-methoxy-6-methyl-1,3,5-triazin-2-yl)aminocarbonyl[aminosulfonyl]benzoic acid, (1-methylethyl)ester: 40%
polyacrylic acid thickener: 0.3%
dodecylphenol polyethylene glycol ether: 0.5%
sodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 16

Solution

4-Chloro-2-[[(4-methoxy-6-methyl-1,3,5-triazin-2-yl)aminocarbonyl]aminosulfonyl]benzoic acid, (1-methylethyl)ester: 5%
water: 95%

The salt is added directly to the water with stirring to produce the solution, which may then be packaged for use.

EXAMPLE 17

Low Strength Granule

4-Chloro-2-[[(4-methoxy-6-methyl-1,3,5-triazin-2-yl)aminocarbonyl]aminosulfonyl]benzoic acid, (1-methylethyl)ester: 0.1%
attapulgite granules (U.S.S. 20–40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

Granule

4-Chloro-2-[[(4-methoxy-6-methyl-1,3,5-triazin-2-yl)aminocarbonyl]aminosulfonyl]benzoic acid, (1-methylethyl)ester: 75%
wetting agent: 1%
crude ligninsulfonate salt (containing 5-20% of the natural sugars): 10%
inert diluent: 14%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

High Strength Concentrate

4-Chloro-2-[[(4-methoxy-6-methyl-1,3,5-triazin-2-yl)aminocarbonyl]aminosulfonyl]benzoic acid, (1-methylethyl)ester: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 20

Wettable Powder

4-Chloro-2-[[(4-methoxy-6-methyl-1,3,5-triazin-2-yl)aminocarbonyl]aminosulfonyl]benzoic acid, (1-methylethyl)ester: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 21

Wettable Powder

4-Chloro-2-[[(4-methoxy-6-methyl-1,3,5-triazin-2-yl)aminocarbonyl]aminosulfonyl]benzoic acid, (1-methylethyl)ester: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 22

Oil Suspension

4-Chloro-2-[[(4-methoxy-6-methyl-1,3,5-triazin-2-yl)aminocarbonyl]aminosulfonyl]benzoic acid, (1-methylethyl)ester: 35%
blend of polyalcohol carboxylic esters and oil soluble petroleum sulfonates: 6%
xylene: 59%

The ingredients are combined and ground together in a sand mill to produce particles essentially all below 5 microns. The product can be used directly, extended with oils, or emulsified in water.

EXAMPLE 23

Dust

4-Chloro-2-[[(4-methoxy-6-methyl-1,3,5-triazin-2-yl)aminocarbonyl]aminosulfonyl]benzoic acid, (1-methylethyl)ester: 10%
attapulgite: 10%
Pyrophyllite: 80%

The active ingredient is blended with attapulgite and then passed through a hammer-mill to produce particles substantially all below 200 microns. The ground concentrate is then blended with powdered pyrophyllite until homogeneous.

EXAMPLE 24

Emulsifiable Concentrate

4-Chloro-2-[[(4-methoxy-6-methyl-1,3,5-triazin-2-yl)aminocarbonyl]aminosulfonyl]benzoic acid, (1-methylethyl)ester 20%
chlorobenzene: 74%
sorbitan monostearate and polyoxyethylene condensates thereof: 6%

The ingredients are combined and stirred to produce a solution which can be emulsified in water for application.

The compound of this invention may be used in combination with other commercial herbicides. Particularly useful combinations would be with the following herbicides.

| Common Name | Chemical Name |
| --- | --- |
| barban | 4-chloro-2-butynyl m-chloro carbanilate |
| benzoylprop ethyl | ethyl N—benzoyl-N—(3,4-dichlorophenyl)-2-aminopropionate |
| bifenox | methyl 5-(2,4-dichlorphenoxy)-2-nitrobenzoate |
| bromofenoxim | 3,5-dibromo-4-hydroxy-benzaldehyde-O—(2',4'-dinitrophenyl)oxime |
| bromoxynil | 3,5-dibromo-4-hydroxy-benzonitrile |
| cyanazine | 2-[[4-chloro-5-(ethylamino)-5-triazin-2-yl]amino-2-methyl-propionitrile |
| diclofop methyl | methyl-2-[(4-(2',4'-dichlorophenoxy)phenoxy]propanoate |
| diallate | S—(2,3-dichloroalkyl)diisopropyl-thiocarbamate |
| difenzoquat | 1,2-dimethyl-3,5-diphenyl-1H—pyrazolium |

| Common Name | Chemical Name |
|---|---|
| diuron | 3-(3,4-dichlorophenyl)-1,1-dimethylurea |
| flamprop methyl | methyl-N—benzoyl-N—(3-chloro-4-fluorophenyl)-2-aminopropioate |
| flamprop isopropyl | isopropyl-N—benzoyl-N—(3-chloro-4-fluorophenyl)-2-aminopropioate |
| ioxynil | 4-hydroxy-3,5-diiodobenzonitrile |
| isoproturon | N—(4-isopropylphenyl)-N',N'—dimethylurea |
| MCPA | [(4-chloro-o-tolyl)oxy]acetic acid |
| mecoprop | 2'-[(4-chloro-o-tolyl)oxy] propionic acid |
| methabenzthiazuron | 1,3-dimethyl-3-(2-benzothiazolyl)urea |
| metribuzin | 4-amino-6-tert-butyl-(3-methylthio)as-triazin-5-(4H)—one |
| metsulfuron methyl | methyl 2[[4-methoxy-6-methyl-1,3,5-triazin-2-yl)aminocarbonyl]aminosulfonyl] benzoate |
| terbutryn | 2-(tert-butylamino)-4-chloro-6-(ethylamino)-S—triazine |
| triallate | S—2,3,3-trichloroallyl)diisopropylthiocarbamate |
| trifluralin | α, α, αtrifluoro-2,6-dinitro-N,N—dipropyl-p-toluidine |
| 2,4-D | (2,4-dichlorophenoxy)acetic acid |
| 3,6-DCP | 3,6-dichloro-2-pyridinecarboxylic acid |
| chlorsulfuron | 2-chloro-N—[(4-methoxy-6-methyl-1,3,5-triazin-2-yl)aminocarbonyl]benzenesulfonamide |
| metoxuron | N—(3-chloro-4-methoxyphenyl)-N,N—dimethylurea |
| propanil | 3',4'-dichlorophenylpropionalide |
| picloram | 4-amino-3,5,6-trichloropicolinic acid |
| — | 4-amino-6-tert-butyl-3-ethylthio-1,2,4-triazin-5(4H)—one |
| — | 2-[(4-amino-3,5-dichloro-6-fluoro-2-pyridinyl)oxy] acetic acid, (1-methylheptyl) ester |

UTILITY

The compound of this invention is particularly useful for the control of blackgrass (*Alopecurus myourides*) in wheat and barley. It also controls many broadleaves and suppresses other grasses in these crops. It may be used either pre or postemergence. Broad application timing and good tolerance make it particularly useful.

Rates needed to provide the desired degree of weed depend on the soil, climate, mode of application, age of crop and weeds, etc. The rate used will vary between about 4 and 125 g/Ha. The exact rate can be selected by one with ordinary skill in the art. This compound may be used with other herbicides that are selective on wheat and barley.

The herbicidal properties of the subject compound were discovered in greenhouse tests. The test below demonstrates the utility of this chemical and its superiority over the two most closely related compounds of U.S. Pat. No. 4,383,113. These data show that the subject compound has a combination of greater activity and selectivity than the two other chemicals.

COMPOUNDS

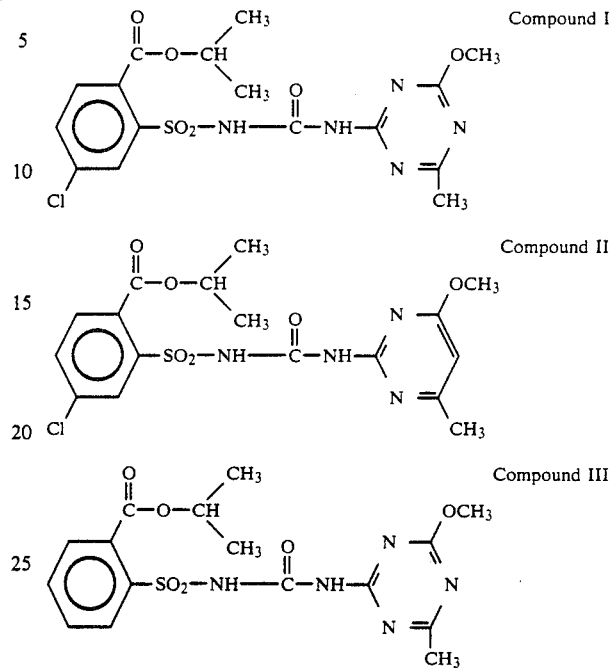

Compound I

Compound II

Compound III

TEST A

Two plastic trays were lined with polyethylene liners and filled with prepared sassafras loamy sand. One tray was planted with wheat (*Triticum aestivum*), barley (*Hordeum vulgare*), wild oat (*Avena fatua*), cheatgrass (*Bromus secalinus*), blackgrass (*Alopecurus myosurides*), Annual bluegrass (*poa annua*), green foxtail (*Setaria viridis*), Italian ryegrass (*Lolium multiflorum*) and rapeseed (*Brassica napus*). The other tray was planted with seeds of Russian thistle (*Salsola kali*), cleavers (*Galium aparine*), speedwell (*Veronica persica*), Kochia (*Kochia scoparia*), shepherdspurse (*Capsella bursa-pastoris*), Matricaria inodora, blacknightshade (*Solanum nigrum*), wild buckwheat (*Polygonum convolvulus*), and sugarbeets (*Beta vulgaris*). The above two trays were treated preemergence. At the same time of application, two trays in which the above plant species were already growing were treated postemergence. Plant heights at the time of treatment ranged from 1–20 cm depending on the plant species.

The compounds applied were diluted with a nonphytotoxic solvent and sprayed over the top of the trays. An untreated control and a solvent alone control were included for comparison. All treatments were maintained in the greenhouse for 19–23 days at which time the treatments were compared to the controls and the effect visually rated. The recorded data are presented in Table A.

The following rating system was used:
0 = no effect
10 = maximum effect
C = chlorosis; and
G = growth retardation

TABLE A

| | RATE kg/ha | | | | |
|---|---|---|---|---|---|
| PRE-EMERGENCE | 0.06 | 0.032 | 0.016 | 0.008 | 0.004 |

TABLE A-continued

COMPOUND NUMBER I

| | | | | | |
|---|---|---|---|---|---|
| Wheat | 0 | 0 | 0 | 0 | 0 |
| Barley | 3G | 1G | 0 | 0 | 0 |
| Wild Oats | 7G | 4G | 2G | 0 | 0 |
| Cheatgrass | 8G | 6G | 5G | 4G | 4G |
| Blackgrass | 9G | 9G | 8G | 8G | 8G |
| Annual Bluegrass | 8G | 8G | 7G | 6G | 5G |
| Green Foxtail | 4G | 3G | 3G | 3G | 3G |
| Italian Ryegrass | 7G | 7G | 5G | 4G | 3G |
| Rapeseed | 10C | 9G | 8G | 8G | 2G |
| Matricaria inodora | 9G | 8G | 8G | 7G | 5G |
| Galium aparine | 10C | 9G | 9G | 9G | 0 |
| Russian Thistle | 8G | 7G | 5G | 2G | 0 |
| Shepherdspurse | 10C | 9G | 9G | 7G | 5G |
| Kochia | 10C | 9G | 8G | 5G | 0 |
| Black Nightshade | 9G | 8G | 6G | 4G | 3G |
| Speedwell | 10C | 10C | 9G | 8G | 8G |
| Wild Buckwheat | 10C | 10C | 5G | 4G | 0 |
| Sugarbeets | 10C | 10C | 9G | 7G | 4G |

COMPOUND NUMBER II

| | | | | | |
|---|---|---|---|---|---|
| Wheat | 2G | 0 | 0 | 0 | 0 |
| Barley | 2G | 1G | 0 | 0 | 0 |
| Wild Oats | 2G | 0 | 0 | 0 | 0 |
| Cheatgrass | 9G | 7G | 7G | 3G | 2G |
| Blackgrass | 10C | 9G | 8G | 7G | 5G |
| Annual Bluegrass | 5G | 5G | 6G | 6G | 4G |
| Green Foxtail | 3G | 0 | 0 | 0 | 0 |
| Italian Ryecrass | 3G | 2G | 0 | 0 | 0 |
| Rapeseed | 9G | 7G | 6G | 5G | 3G |
| Matricaria inodora | 8G | 8G | 7G | 5G | 2G |
| Galium aprine | 10C | 10C | 0 | 0 | 0 |
| Russian Thistle | 8G | 7G | 7G | 4G | 2G |
| Shepherdspurse | 10C | 8G | 9G | 8G | 6G |
| Kochia | 7G | 5G | 5G | 2G | 0 |
| Speedwell | 10C | 8G | 5G | 5G | 5G |
| Black Nightshade | 0 | 0 | 0 | 0 | 0 |
| Wild Buckwheat | 9G | 9G | 8G | 5G | 0 |
| Sugarbeets | 5G | 4G | 4G | 0 | 0 |

COMPOUND NUMBER III

| | | | | | |
|---|---|---|---|---|---|
| Wheat | 0 | 0 | 0 | 0 | 0 |
| Barley | 0 | 0 | 0 | 0 | 0 |
| Wild Oats | 2G | 2G | 0 | 0 | 0 |
| Cheatgrass | 5G | 4G | 2G | 0 | 0 |
| Blackgrass | 7G | 6G | 6G | 4G | 2G |
| Annual Bluegrass | 5G | 5G | 4G | 4G | 3G |
| Green Foxtail | 2G | 0 | 0 | 0 | 0 |
| Italian Ryegrass | 5G | 3G | 2G | 0 | 0 |
| Rapeseed | 10C | 9G | 9G | 9G | 9G |
| Matricaria inodora | 9G | 9G | 9G | 8G | 6G |
| Galium aparine | 10C | 10C | 10C | 10C | 0 |
| Russian Thistle | 9G | 8G | 8G | 6G | 2G |
| Shepherdspurse | 10C | 9G | 9G | 8G | 7G |
| Kochia | 10C | 8G | 6G | 6G | 4G |
| Black Nightshade | 9G | 8G | 7G | 7G | 3G |
| Speedwell | 10C | 10C | 10G | 10C | 8G |
| Buckwheat | 10C | 9G | 8G | 7G | 4G |
| Sugarbeets | 10C | 10C | 9G | 9G | 8G |

| POST-EMERGENCE | RATE kg/ha | | | | |
|---|---|---|---|---|---|
| | 0.06 | 0.032 | 0.016 | 0.008 | 0.004 |

COMPOUND NUMBER I

| | | | | | |
|---|---|---|---|---|---|
| Wheat | 0 | 0 | 0 | 0 | 0 |
| Barley | 2G | 0 | 0 | 0 | 0 |
| Wild Oats | 2G | 0 | 0 | 0 | 0 |
| Cheatgrass | 8G | 7G | 4G | 2G | 0 |
| Blackgrass | 10C | 10C | 7G | 7G | 4G |
| Annual Bluegrass | 7G | 7G | 5G | 5G | 2G |
| Green Foxtail | 3G | 2G | 0 | 0 | 0 |
| Italian Ryegrass | 8G | 7G | 4G | 4G | 3G |
| Rapeseed | 10C | 10C | 10C | 10C | 10C |
| Matricaria inodora | 10C | 10C | 10C | 10C | 10C |
| Galium aparine | 10C | 10C | 9G | 5G | 5G |
| Russian Thistle | 10C | 10C | 10C | 10C | 10C |
| Shepherdspurse | 10C | 10C | 10C | 10C | 10C |
| Kochia | 10C | 10C | 10C | 8G | 6G |
| Black Nightshade | 9G | 9G | 8G | 5G | 4G |
| Speedwell | 10C | 10C | 10C | 8G | 8G |
| Wild Buckwheat | 10C | 10C | 9G | 9G | 7G |
| Sugarbeets | 10C | 10C | 10C | 10C | 10C |

COMPOUND NUMBER II

| | | | | | |
|---|---|---|---|---|---|
| Wheat | 0 | 0 | 0 | 0 | 0 |
| Barley | 2G | 2G | 0 | 0 | 0 |
| Wild Oats | 0 | 0 | 0 | 0 | 0 |
| Cheatgrass | 9G | 8G | 7G | 5G | 3G |
| Blackgrass | 9G | 9G | 8G | 5G | 2G |
| Annual Bluegrass | 5G | 5G | 3G | 2G | 0 |
| Green Foxtail | 0 | 0 | 0 | 0 | 0 |
| Italian Ryegrass | 6G | 3G | 0 | 0 | 0 |
| Rapeseed | 10C | 10C | 10C | 9G | 9G |
| Matricaria inodora | 10C | 10C | 9G | 9G | 7G |
| Galium aparine | 10 | 10 | 6G | 6G | 5G |
| Russian Thistle | 10C | 10C | 10C | 9G | 7G |
| Shepherdspurse | 10C | 10C | 10C | 9G | 8G |
| Kochia | 10C | 0 | 0 | 0 | 0 |
| Black Nightshade | 2G | 2G | 0 | 0 | 0 |
| Speedwell | 10C | 10C | 7G | 7G | 7G |
| Wild Buckwheat | 7G | 7G | 5G | 3G | 0 |
| Sugarbeets | 7G | 7G | 3G | 3G | 3G |

COMPOUND NUMBER III

| | | | | | |
|---|---|---|---|---|---|
| Wheat | 0 | 0 | 0 | 0 | 0 |
| Barley | 0 | 0 | 0 | 0 | 0 |
| Wild Oats | 0 | 0 | 0 | 0 | 0 |
| Cheatgrass | 5G | 2G | 2G | 0 | 0 |
| Blackgrass | 8G | 8G | 5G | 4G | 2G |
| Annual Bluegrass | 5G | 3G | 2G | 0 | 0 |
| Green Foxtail | 0 | 0 | 0 | 0 | 0 |
| Italian Ryegrass | 4G | 4G | 2G | 0 | 0 |
| Rapeseed | 10C | 10C | 10C | 10C | 10C |
| Matricaria inodora | 10C | 10C | 10C | 10C | 10C |
| Galium aparine | 10C | 9G | 9G | 9G | 9G |
| Russian Thistle | 10C | 10C | 10C | 10C | 10C |
| Shepherdspurse | 10C | 10C | 10C | 10C | 10C |
| Kochia | 10C | 10C | 10C | 10C | 10C |
| Black Nightshade | 8G | 8G | 3G | 1G | 0 |
| Speedwell | 10C | 10C | 10C | 10C | 8G |
| Wild Buckwheat | 10C | 10C | 10C | 8G | 7G |
| Sugarbeets | 10C | 10C | 10C | 10C | 10C |

What is claimed is:

1. A compound selected from 4-chloro-2-[[(4-methoxy-6-methyl-1,3,5-triazin-2-yl)aminocarbonyl-]aminosulfonyl]benzoic acid (1-methylethyl)ester and its agriculturally suitable salts.

2. The compound of claim 1 that is 4-chloro-2-[[(4-methoxy-6-methyl-1,3,5-triazin-2-yl)aminocarbonyl]-aminosulfonyl]benzoic acid (1-methylethyl)ester.

3. A composition suitable for controlling the growth of undesired vegetation which comprises an effective amount of the compound of claim 2 and at least one of the following: surfactant, solid or liquid diluent.

4. A method for controlling the growth of undesired vegetation which comprises applying to the locus to be protected an effective amount of a compound of claim 2.

5. The method of claim 4 where the vegetation is blackgrass.